US009192650B2

(12) United States Patent
Zacks et al.

(10) Patent No.: US 9,192,650 B2
(45) Date of Patent: Nov. 24, 2015

(54) METHODS OF INHIBITING PHOTORECEPTOR APOPTOSIS BY ELICITING THE FAIM2 ANTIAPOPTOTIC PATHWAY

(75) Inventors: David N. Zacks, Ann Arbor, MI (US); Cagri Besirli, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/599,699

(22) Filed: Aug. 30, 2012

(65) Prior Publication Data
US 2013/0053328 A1 Feb. 28, 2013

Related U.S. Application Data

(60) Provisional application No. 61/529,106, filed on Aug. 30, 2011.

(51) Int. Cl.
*A61K 48/00* (2006.01)
*A61P 27/02* (2006.01)
*A61K 38/17* (2006.01)
*A01K 67/027* (2006.01)
*C07H 21/04* (2006.01)
*C07K 14/705* (2006.01)
*C12N 15/861* (2006.01)

(52) U.S. Cl.
CPC ............ *A61K 38/1709* (2013.01); *A01K 67/027* (2013.01); *A61K 48/0066* (2013.01); *A61K 48/0075* (2013.01); *A01K 2207/30* (2013.01); *A01K 2227/105* (2013.01); *A01K 2267/03* (2013.01); *A61K 48/00* (2013.01); *C07H 21/04* (2013.01); *C07K 14/705* (2013.01); *C12N 15/861* (2013.01)

(58) Field of Classification Search
None
See application file for complete search history.

(56) References Cited

U.S. PATENT DOCUMENTS 6,500,940 B1 * 12/2002 Verma et al. ................. 536/23.5
8,470,790 B2    6/2013 Pan et al.

OTHER PUBLICATIONS

Record for NP_036438, NCBI Protein Database, 5 pages as printed on Apr. 17, 2013.*
Besirli et al (2012. PLOS ONE. 7(9): 1-9).*
Boyaka et al (2009. FASEB Journal. 23:3743-3751).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Carvalho et al, 2014 (Vision Research; pp. 1-10).*
Daya et al, 2008. Clinical Microbiology Reviews. 21(4): 583-593.*
Beier et al. "FasL (CD95L/APO-1L) resistance of neurons mediated by phosphatidylinositol 3-kinase-Akt/protein kinase B-dependent expression of lifeguard/neuronal membrane protein 35." J Neurosci 2005; 25:6765-6774.
Bennett, "Adenovirus-mediated delivery of rhodopsin-promoted bcl-2 results in a delay in photoreceptor cell death in the rd/rd mouse." Gene Therapy 1998, 5:1156-1164.
Besirli et al. "Autophagy activation in the injured photoreceptor inhibits fas-mediated apoptosis." Invest Ophthalmol Vis Sci. Jun. 13, 2011; 52(7):4193-9.
Besirli et al. "Inhibition of retinal detachment-induced apoptosis in photoreceptors by a small peptide inhibitor of the fas receptor." Invest Ophthalmol Vis Sci 2010;51:2177-2184.
Bourges et al."Intraocular implants for extended drug delivery: therapeutic applications." Adv Drug Deliv Rev. Nov. 15, 2006;58(11):1182-202.
Burton "Recovery of visual acuity after retinal detachment involving the macula." Trans Am Ophthalmol Soc. 1982; 80:475-497.
Chong et al. "Interleukin-6 as a photoreceptor neuroprotectant in an experimental model of retinal detachment." Invest Ophthalmol Vis Sci 2008; 49:3193-3200.
Cook et al. "Apoptotic photoreceptor degeneration in experimental retinal detachment." Invest Ophthalmol Vis Sci. 1995; 36(6):990-996.
Fernandez et al., "Lifeguard/neuronal membrane protein 35 regulates Fas ligand-mediated apoptosis in neurons via microdomain recruitment." Journal of Neurochemistry, 2007, 103:190-203.
Ghate & Edelhauser. "Ocular drug delivery." Expert Opin Drug Deliv. Mar. 2006; 3(2):275-87.
Gomes Dos Santos et al. "Intraocular delivery of oligonucleotides." Curr Pharm Biotechnol. Feb. 2005; 6(1):7-15.
Hassan et al. "The effect of duration of macular detachment on results after the scleral buckle repair of primary, macula-off retinal detachments." Ophthalmology 2002; 109(1):146-152.
Hisatomi et al. "Critical role of photoreceptor apoptosis in functional damage after retinal detachment." Curr Eye Res. 2002;24(3):161-172.
Hu et al. "LFG: a candidate apoptosis regulatory gene family." Apoptosis 2009; 14:1255-1265.
Janoria et al. "Novel approaches to retinal drug delivery." Expert Opinion on Drug Delivery. Expert Opin Drug Deilv. Jul. 2007; 4(4):371-88.
Mielke & Herdegen. "JNK and p38 stresskinases—degenerative effectors of signal-transduction-cascades in the nervous system." Prog Neurobiol 2000; 61:45-60.
Miyoshi et al., "Stable and efficient gene transfer into the retina using an HIV-based lentiviral vector." Proc. Natl. Acad. Sci. Sep. 1997, 94: 10319-10323.

(Continued)

*Primary Examiner* — Zachary Howard
(74) *Attorney, Agent, or Firm* — Casimir Jones, S.C.

(57) ABSTRACT

The present invention provides compositions and methods to prevent apoptosis. In particular, provided herein are compositions and methods which prevent FAS-mediated photoreceptor apoptosis.

13 Claims, 7 Drawing Sheets

(56) References Cited

OTHER PUBLICATIONS

Nozaki et al. "gen-activated protein kinases and cerebral ischemia." Mol Neurobiol 2001; 23:1-19.
Piccolino et al. "The foveal photoreceptor layer and visual acuity loss in central serous chorioretinopathy." Am J Ophthalmol 2005; 139:87-99.
Raoul et al. "Active killing of neurons during development and following stress: a role for p75(NTR) and Fas?" Curr Opin Neurobiol 2000; 10:111-117.
Reich et al. "Fas/CD95 regulatory protein Faim2 is neuroprotective after transient brain ischemia." J Neurosci 2011; 31:225-233.
Reimers et al. "Sequence analysis shows that Lifeguard belongs to a new evolutionarily conserved cytoprotective family." Int J Mol Med 2006; 18:729-734.
Ross & Stockl. "Visual recovery after retinal detachment." Curr Opin Ophthalmol 2000; 11:191-194.
Ross et al. "Visual recovery in macula-off rhegmatogenous retinal detachments." Ophthalmology 1998; 105 (11):2149-2153.
Ross. "Visual recovery after macula-off retinal detachment." Eye (Lond) 2002; 16: 440-446.
Somia et al. "LFG: an anti-apoptotic gene that provides protection from Fas-mediated cell death." Proc Natl Acad Sci U S A 1999; 96:12667-12672.
Tan et al. "Expression of cone-photoreceptor-specific antigens in a cell line derived from retinal tumors in transgenic mice." Investigative ophthalmology & Visual science 2004; 45:764-768.
Xue et al. "GPS: a comprehensive www server for phosphorylation sites prediction." Nucleic Acids Res 2005; 33: W184-187.
Yang et al. Invest Ophthalmol Vis Sci. "Preventing retinal detachment-associated photoreceptor cell loss in Bax-deficient mice." 2004; 45(2):648-654.
Zacks et al. "Caspase activation in an experimental model of retinal detachment." Invest Ophthalmol Vis Sci. 2003; 44 (3):1262-1267.
Zacks et al. "FAS-mediated apoptosis and its relation to intrinsic pathway activation in an experimental model of retinal detachment." Invest Ophthalmol Vis Sci 2004; 45:4563-4569.
Zacks et al. "Role of the Fas-signaling pathway in photoreceptor neuroprotection." Arch Ophthalmol 2007; 125:1389-1395.
Zacks. "Gene transcription profile of the detached retina (An AOS Thesis)." Trans Am Ophthalmol Soc 2009; 107:343-382.
Zadro-Lamoureux et al. "XIAP effects on retinal detachment-induced photoreceptor apoptosis [corrected]." Investigative Ophthalmology & Visual Science, Mar. 2009;50(3):1448-53.

* cited by examiner

A

B

A

B

C

SEQUENCE LISTING

<160> NUMBER OF SEQ ID NOS: 1

<210> SEQ ID NO 1
<211> LENGTH: 316
<212> TYPE: PRT
<213> ORGANISM: Homo sapiens

```
<400> SEQUENCE: 1

Met Thr Gln Gly Lys Leu Ser Val Ala Asn Lys Ala Pro Gly Thr Glu
1               5                   10                  15

Gly Gln Gln Gln Val His Gly Glu Lys Lys Glu Ala Pro Ala Val Pro
                20                  25                  30

Ser Ala Pro Pro Ser Tyr Glu Glu Ala Thr Ser Gly Glu Gly Met Lys
            35                  40                  45

Ala Gly Ala Phe Pro Pro Ala Pro Thr Ala Val Pro Leu His Pro Ser
    50                  55                  60

Trp Ala Tyr Val Asp Pro Ser Ser Ser Ser Tyr Asp Asn Gly Phe
65                  70                  75                  80

Pro Thr Gly Asp His Glu Leu Phe Thr Thr Phe Ser Trp Asp Asp Gln
                85                  90                  95

Lys Val Arg Arg Val Phe Val Arg Lys Val Tyr Thr Ile Leu Leu Ile
                100                 105                 110

Gln Leu Leu Val Thr Leu Ala Val Val Ala Leu Phe Thr Phe Cys Asp
            115                 120                 125

Pro Val Lys Asp Tyr Val Gln Ala Asn Pro Gly Trp Tyr Trp Ala Ser
    130                 135                 140

Tyr Ala Val Phe Phe Ala Thr Tyr Leu Thr Leu Ala Cys Cys Ser Gly
145                 150                 155                 160

Pro Arg Arg His Phe Pro Trp Asn Leu Ile Leu Leu Thr Val Phe Thr
                165                 170                 175

Leu Ser Met Ala Tyr Leu Thr Gly Met Leu Ser Ser Tyr Tyr Asn Thr
            180                 185                 190

Thr Ser Val Leu Leu Cys Leu Gly Ile Thr Ala Leu Val Cys Leu Ser
        195                 200                 205

Val Thr Val Phe Ser Phe Gln Thr Lys Phe Asp Phe Thr Ser Cys Gln
    210                 215                 220

Gly Val Leu Phe Val Leu Leu Met Thr Leu Phe Phe Ser Gly Leu Ile
225                 230                 235                 240

Leu Ala Ile Leu Leu Pro Phe Gln Tyr Val Pro Trp Leu His Ala Val
                245                 250                 255

Tyr Ala Ala Leu Gly Ala Gly Val Phe Thr Leu Phe Leu Ala Leu Asp
            260                 265                 270

Thr Gln Leu Leu Met Gly Asn Arg Arg His Ser Leu Ser Pro Glu Glu
        275                 280                 285

Tyr Ile Phe Gly Ala Leu Asn Ile Tyr Leu Asp Ile Ile Tyr Ile Phe
    290                 295                 300

Thr Phe Phe Leu Gln Leu Phe Gly Thr Asn Arg Glu
305                 310                 315
```

METHODS OF INHIBITING PHOTORECEPTOR APOPTOSIS BY ELICITING THE FAIM2 ANTIAPOPTOTIC PATHWAY

CROSS-REFERENCE TO RELATED APPLICATIONS

The present application claims priority to pending U.S. Provisional Patent Application No. 61/529,106, filed Aug. 30, 2011, the contents of which are incorporated by reference in its entirety.

GOVERNMENT SUPPORT

This invention was made with government support under EY020823 awarded by the National Institutes of Health. The government has certain rights in the invention.

FIELD OF THE INVENTION

The present invention provides compositions and methods to prevent apoptosis. In particular, provided herein are compositions and methods which prevent FAS-mediated photoreceptor apoptosis.

BACKGROUND OF THE INVENTION

Apoptosis (programmed cell death) plays a central role in the development and homeostasis of all multi-cellular organisms. Alterations in apoptotic pathways have been implicated in many types of human pathologies, including developmental disorders, cancer, autoimmune diseases, as well as neurodegenerative disorders, and retinal degradation. It is a tightly regulated pathway governing the death processes of individual cells and can be initiated either extrinsically or intrinsically. The latter is an intracellular mechanism triggered by the mitochondria while the former involves the interaction of a 'death receptor' with its corresponding ligand at the cell membrane.

Thus, the programmed cell death pathways have become attractive targets for development of therapeutic agents. In particular, since it is conceptually easier to kill cells than to sustain cells, attention has been focused on anti-cancer therapies using pro-apoptotic agents such as conventional radiation and chemotherapy. These treatments are generally believed to trigger activation of the mitochondria-mediated apoptotic pathways. However, these therapies lack molecular specificity, and more specific molecular targets are needed.

Retinal detachment (RD), defined as the separation of the neurosensory retina from subjacent retinal pigment epithelium (RPE), results in the apoptotic death of photoreceptor cells (Cook et al. 1995; 36(6):990-996; Hisatomi et al. Curr Eye Res. 2002; 24(3):161-172; Zacks et al. Invest Ophthalmol Vis Sci. 2003; 44(3):1262-1267. Yang et al. Invest Ophthalmol Vis Sci. 2004; 45(2):648-654; herein incorporated by reference in their entireties). Rodent and feline models of RD have demonstrated the activation of pro-apoptotic pathways nearly immediately after the retina becomes separated from the RPE (Cook et al. 1995; 36(6):990-996; Hisatomi et al. Curr Eye Res. 2002; 24(3):161-172; Zacks et al. Invest Ophthalmol Vis Sci. 2003; 44(3):1262-1267. Yang et al. Invest Ophthalmol Vis Sci. 2004; 45(2):648-654; herein incorporated by reference in their entireties). Histological markers of apoptosis such as terminal deoxynucliotidyl transferase nick end label (TUNEL) staining reach a peak at approximately three days after RD, with apoptotic activity and progressive cell death persisting for the duration of the detachment period. Clinical experience in the repair of retinal detachments, however, has demonstrated that there is a window of opportunity for repair with preservation of good visual acuity. Retrospective case series have demonstrated that significant numbers of patients with macula-off RDs repaired within 5-10 days after onset of detachment can retain relatively good visual function, but that the visual acuity drops significantly as the time between detachment and repair extends (Burton. Trans Am Ophthalmol Soc. 1982; 80:475-497; Ross et al. Ophthalmology. 1998; 105(11):2149-2153; Hassan et al. Ophthalmology. 2002; 109(1):146-152; herein incorporated by reference in their entireties). The delayed time between the activation of pro-apoptosis pathways and the clinical onset of visual loss suggests that intrinsic neuroprotective factors may become activated within the neural retina, and may serve to counter-balance the effects of the pro-apoptotic pathways activated by retinal-RPE separation.

SUMMARY

In some embodiments, the present invention provides a method of increasing photoreceptor survival comprising administering a composition that elicits the Faim2 antiapoptotic pathway. In some embodiments, increasing photoreceptor survival comprises inhibiting photoreceptor apoptosis. In some embodiments, administering a composition that elicits the Faim2 antiapoptotic pathway comprises administering a Faim2 polypeptide or peptide. In some embodiments, administering a Faim2 polypeptide or peptide comprises directly administering a Faim2 polypeptide or peptide or administering a nucleic acid encoding a Faim2 polypeptide or peptide. In some embodiments, the Faim2 polypeptide or peptide comprises full-length Faim2 or a fragment of full-length Faim2. In some embodiments, the Faim2 polypeptide or peptide comprises one or more mutations (e.g., 1, 2, 3, 4, 5, 6, 7, 8, 9, 10 . . . 20 . . . 30 . . . 40 . . . 50, etc.) with respect to wild-type Faim2 or a fragment thereof. In some embodiments, the Faim2 polypeptide or peptide has greater than 70% sequence identity with wild-type Faim2 or a fragment thereof. In some embodiments, Faim2 polypeptide or peptide comprises full-length Faim2. In some embodiments, the Faim2 polypeptide or peptide comprises a fragment of full-length Faim2. In some embodiments, the fragment of full-length Faim2 maintains anti-apoptoitic and/or photoreceptor protective functionality of full-length Faim2. In some embodiments, the fragment of full-length Faim2 is less than 100 amino acids in length. In some embodiments, the fragment of full-length Faim2 is less than 50 amino acids in length. In some embodiments, the fragment of full-length Faim2 is less than 20 amino acids in length. In some embodiments, photoreceptor apoptosis comprises FAS-mediated photoreceptor apoptosis. In some embodiments, the photoreceptor protective composition is administered to a population of cells. In some embodiments, the photoreceptor protective composition is administered in an amount sufficient to enhance photoreceptor survival within the population of cells. In some embodiments, the photoreceptor protective composition is administered to a subject. In some embodiments, the subject is at risk of an ocular condition, disease, or condition or disease affecting ocular health. In some embodiments, the subject suffers from an ocular condition, disease, or condition or disease affecting ocular health. In some embodiments, the ocular condition, disease, or condition or disease affecting ocular health comprises retinal detachment, macular degeneration, retinitis pigmentosa, occular inflammation, autoimmune retinopathy, trauma, cancer, tumor, uveitis, hereditary retinal degeneration, diabetic retinopathy, choroidal neovascularization, retinal ischemia, pathologic myopia, angioid streaks, macular edema, or central serous chorioretinopathy. In some embodiments, the ocular condition, disease, or condition or disease affecting ocular health comprises retinal detachment. In some embodiments, the ocular condition, disease, or condition or disease affecting ocular health comprises macular degeneration. In some embodiments, administering a composition that elicits the Faim2 antiapoptotic pathway comprises administering a composition that regulates Faim2 expression, activity, transport, clearance, or degradation. In some embodiments, administering a composition that elicits the Faim2 antiapoptotic pathway comprises administering a composition to activate or inhibit a regulator of Faim2. In some embodiments, the regulator of Faim2 is part of the ERK pathway. In some embodiments, the regulator of Faim2 comprises ERK.

In some embodiments, the present invention provides a composition comprising a photoreceptor protective composition and a pharmaceutical carrier configured for optical delivery, wherein the photoreceptor protective composition that elicits the Faim2 antiapoptotic pathway. In some embodiments, the photoreceptor protective composition comprises a photoreceptor protective polypeptide, or a nucleic acid encoding a photoreceptor protective polypeptide. In some embodiments, the photoreceptor protective polypeptide comprises Faim2 of a portion thereof. In some embodiments, the Faim2 polypeptide or peptide comprises full-length Faim2. In some embodiments, the Faim2 polypeptide or peptide comprises a fragment of full-length Faim2. In some embodiments, the fragment of full-length Faim2 maintains anti-apoptoitic and/or photoreceptor protective functionality of full-length Faim2. In some embodiments, the fragment of full-length Faim2 is less than 100 amino acids in length. In some embodiments, the fragment of full-length Faim2 is less than 50 amino acids in length. In some embodiments, the fragment of full-length Faim2 is less than 20 amino acids in length.

In some embodiments, the present invention provides a Faim2 polypeptide (full length or fragment) for use as a medicament. In some embodiments, the Faim2 polypeptide finds use as a medicament for the treatment of an ocular disease or condition (e.g., macular degeneration; tissue damage associated with retinal detachment; etc.).

BRIEF DESCRIPTION OF THE DRAWINGS

The summary and detailed description are better understood when read in conjunction with the accompanying drawings which are included by way of example and not by way of limitation.

DEFINITIONS

Figure 1:
FIG. 1A shows Retina-RPE separation leads to increased Faim2 expression. Western blots showing increased levels of Faim2 as a function of time after retina-RPE separation. Equal amounts of protein were loaded in each lane.
FIG. 1B shows Faim2 levels are elevated in 661W photoreceptor cells upon activation of Fas signaling. 661W cells treated with 500 ng/mL of Fas-activating antibody (Fas-AAb, +) show increased levels of Faim2 protein. Cells were treated for 4 hours, lysed and protein expression was analyzed via immunoblotting. Control cells were not treated with Fas-AAb (−). Actin is shown as loading control.
Figure 1:
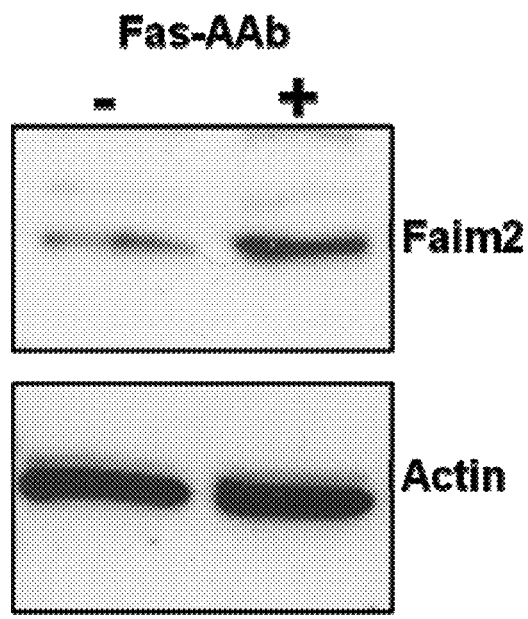

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 12 residue oligonucleotide is referred to as a "12-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "effective amount" refers to the amount of a composition (e.g., photoreceptor protective composition) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) (e.g., photoreceptor protective peptides, oligonucleotides coding for a photoreceptor protective composition, and one or more other agents) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "pharmaceutical composition" refers to the combination of an active agent (e.g., photoreceptor protective composition) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

DETAILED DESCRIPTION OF EMBODIMENTS

Separation of outer retina from the retinal pigment epithelium (RPE) is a common form of injury that may occur alone in retinal detachment or with other pathologic processes in many blinding diseases such as age-related macular degeneration or diabetic retinopathy. Despite significant advances in the medical and surgical management of retina-RPE separation, patients often lose vision, primarily due to the death of photoreceptors (Burton. *Trans Am Ophthalmol Soc* 1982; 80:475-497; Piccolino et al. *Am J Ophthalmol* 2005; 139:87-99; herein incorporated by reference in their entireties). The main pathologic event causing photoreceptor death is the activation of the apoptotic Fas signaling and the downstream cascade of caspases 8, 3, 7 and 9 (Zacks et al. *Arch Ophthalmol* 2007; 125:1389-1395; Zacks et al. *Invest Ophthalmol Vis Sci* 2003; 44:1262-1267; Zacks et al. *Invest Ophthalmol Vis Sci* 2004; 45:4563-4569; herein incorporated by reference in their entireties). Preventing Fas pathway activity provides significant protection against separation-induced death of the photoreceptors.

Experimental data from animal models demonstrates that despite rapid activation of apoptosis after retina-RPE separation, a significant number of photoreceptors survive for extended periods of time. The clinical correlation of this experimental observation is that patients with retinal detachments affecting central vision generally recover near-normal vision if the detachment is repaired within one week (Ross. *Eye (Lond)* 2002; 16:440-446; Ross & Stockl. *Curr Opin Ophthalmol* 2000; 11:191-194; herein incorporated by reference in their entireties). If repair is delayed beyond one week, visual outcomes become significantly poorer. These experimental and clinical observations suggest that early in the course of retinal detachment, anti-apoptotic pathways are activated within the retina to counteract the effect of pro-apoptotic signals and that they are responsible for the therapeutic window-of-opportunity for reattachment. The existence of two such pathways in the retina has been demonstrated, IL-6 signaling and autophagy (Besirli et al. *Invest Ophthalmol Vis Sci* 2011; Chong et al. *Invest Ophthalmol Vis Sci* 2008; 49:3193-3200; herein incorporated by reference in their entireties).

In some embodiments, the present invention provides a method of increasing photoreceptor survival comprising administering a composition that elicits the Fas apoptotic inhibitory molecule 2 (Faim2; NP_036438) antiapoptotic pathway. Faim2 is evolutionarily conserved and is predominantly expressed in neuronal cells as a 35 kDa membrane protein. Faim2 belongs to a larger group of evolutionary conserved anti-apoptotic proteins known as Lifeguard (LFG) family (Hu et al. *Apoptosis* 2009; 14:1255-1265; herein incorporated by reference in its entirety). Faim2 prevents apoptosis by direct interaction with Fas upstream of Fas-associated death domain containing protein (FADD) (Somia et al. *Proc Natl Acad Sci USA* 1999; 96:12667-12672; herein incorporated by reference in its entirety). Faim2 expression in cerebellar granule neurons increases their resistance to Fas mediated apoptosis (Beier et al. *J Neurosci* 2005; 25:6765-6774; herein incorporated by reference in its entirety). Neurons of Faim2-deficient mice are more susceptible to combined oxygen-glucose deprivation in vitro and caspase-associated cell death and neurological impairment after cerebral ischemia in vivo (Reich et al. *J Neurosci* 2011; 31:225-233; herein incorporated by reference in its entirety).

A set of genes that were upregulated in microarray analysis of experimental detachments in rats were downstream targets of Mitogen-Activated Protein Kinase (MAPK) superfamily (Zacks. *Trans Am Ophthalmol Soc* 2009; 107:343-382; herein incorporated by reference in its entirety). The MAPK superfamily is composed of three major sets of kinases: the extracellular-receptor kinases (ERK), the c-Jun N-terminal kinases (JNK) and the p38 MAPKs (Nozaki et al. *Mol Neurobiol* 2001; 23:1-19; herein incorporated by reference in its entirety). Neuronal injury models suggest that stress kinase signaling is involved in Fas-receptor activation (Mielke & Herdegen. *Prog Neurobiol* 2000; 61:45-60; Raoul et al. *Curr Opin Neurobiol* 2000; 10:111-117; herein incorporated by reference in their entireties). Members of the MAPK superfamily have been shown to be critical for cell survival as well as cell death in many models of apoptotic and non-apoptotic cell death and their role largely depends on the context and cellular insult.

Experiments conducted during development of embodiments of the present invention demonstrated that increased Faim2 expression after retina-RPE separation prevents photoreceptor apoptosis. The role of Faim2 expression and MAPK signaling during photoreceptor apoptosis was analyzed using an in vivo model of experimental retinal detachment and an in vitro model using 661W photoreceptor cells. Results demonstrate that retinal detachment increases Faim2 protein levels in vivo. This finding is reproduced in vitro by exogenous activation of Fas signaling in 661W cells. Fas-signaling also leads to increased activity of ERK and JNK kinases in 661W cells. The expression of Faim2 is regulated by ERK signaling as pharmacological inhibition of ERK activity reduces Faim2 levels. The inhibition of ERK signaling results in more robust activation of caspases and leads to increased Fas-mediated photoreceptor cell death. This effect is mediated, at least in part, by decreased levels Faim2 in cells, as siRNA knock-down of Faim2 protein enhances caspase 8 activity after Fas receptor activation.

In some embodiments, the present invention provides compositions (e.g., Faim2 polypeptides, and portions thereof (e.g., Faim2 fragments)) that autoregulate Fas-mediated apoptosis and increase photoreceptor survival (SEE FIG. 7).

Experiments were conducted during development of embodiments of the present invention to demonstrate that Faim2 expression is increased after retina-RPE separation and is induced by Fas receptor activation via ERK stress-kinase pathway signaling. Blocking ERK pathway reduces Faim2 levels and increases caspase activity and photoreceptor death after Fas receptor activation.

Activation of the Fas death receptor signaling is the primary event causing photoreceptor apoptosis after the separation of the neurosensory retina from the underlying RPE (Zacks et al. *Arch Ophthalmol* 2007; 125:1389-1395; Zacks et al. *Invest Ophthalmol Vis Sci* 2003; 44:1262-1267; Zacks et al. *Invest Ophthalmol Vis Sci* 2004; 45:4563-4569; herein incorporated by reference in their entireties). Molecular or pharmacological interventions that prevent Fas receptor activation or transcription of new Fas receptor provide significant protection against the separation-induced death of the photoreceptors (Zacks et al. *Arch Ophthalmol* 2007; 125:1389-1395; Besirli et al. *Invest Ophthalmol Vis Sci* 2010; 51:2177-2184; herein incorporated by reference in their entireties). Although the biochemical markers of Fas activation are detected shortly after retina-RPE separation, significant numbers of photoreceptors can survive for extended periods of time. Experiments conducted during development of embodiments of the present invention demonstrate that Faim2 is an anti-apoptotic molecule activated in detached photoreceptors.

Faim2 is an evolutionarily conserved protein and predicted to have seven transmembrane domains and a small cytoplasmic domain at the N-terminus (Reimers et al. *Int J Mol Med* 2006; 18:729-734; herein incorporated by reference in its entirety). Faim2 interacts with Fas receptor directly, but it does not bind downstream effectors of Fas signaling such as FADD or interfere with binding of Fas agonists (Somia et al. *Proc Natl Acad Sci USA* 1999; 96:12667-12672; herein incorporated by reference in its entirety). Knock-down experiments with siRNA against Faim2 demonstrate that caspase 8 activation is regulated by Faim2. Since caspase 8 cleavage is a proximal event in Fas death receptor signaling, this knock-down data further indicate direct Faim2-Fas receptor interaction.

Fas signaling is critical to photoreceptor apoptosis after retinal detachment. Unexpectedly, direct activation of Fas receptor with an activating antibody causes rapid increase in Faim2 levels in photoreceptor cells. This reveals an unknown autoregulatory mechanism of apoptotic Fas receptor signaling. In photoreceptor cells, Fas signaling triggers this autoregulatory pathway by activating ERK. ERK then up regulates Faim2. ERK either regulates Faim2 expression through increased gene transcription, stabilizing Faim2 mRNA, or slowing down Faim2 protein degradation. An understanding of the particular mechanism of action is not needed to practice the invention, nor is the invention limited to any particular underlying mechanism of action.

In addition to ERK, the induction of Fas receptor signaling in photoreceptor cells activates JNK stress-kinase pathway. Experiments conducted during development of embodiments of the present invention demonstrate that while ERK signaling was important in regulating Faim2 expression, inhibiting JNK activity with SP600125 did not have any effect on Faim2 levels. However, JNK inhibition in Fas-treated cells caused increased caspase activation and cell death, indicating that JNK activity is an important survival mechanism in photoreceptors after Fas exposure.

Experiments conducted during development of embodiments of the present invention indicate that Faim2 is subject to post-translational modification in Fas-exposed photoreceptor cells. The analysis of mouse Faim2 amino acid sequence reveals a potential JNK phosphorylation target located in the C-terminus between predicted transmembrane domains 6 and 7 (amino acid 286) (Xue et al. *Nucleic Acids Res* 2005; 33:W184-187; herein incorporated by reference in its entirety). This sequence motif is evolutionary conserved among different mammalian and non-mammalian species (Reimers et al. *Int J Mol Med* 2006; 18:729-734; herein incorporated by reference in its entirety).

Experiments conducted during development of embodiments of the present invention demonstrate a novel autoregulatory mechanism of Fas receptor signaling during photoreceptor apoptosis. This autoregulation is mediated by differential expression of Faim2 and is important for photoreceptor survival. ERK stress-kinase signaling acts upstream of Faim2. Therapeutic interventions targeting photoreceptor ERK pathway to modulate Faim2 expression may be used to prevent photoreceptor apoptosis after retina-RPE separation.

In some embodiments, the present invention provides compositions, kits, systems, and/or methods to prevent, inhibit, block, and/or reduce photoreceptor cell death (e.g., in a human subject in need thereof). In some embodiments, the present invention inhibits apoptosis of photoreceptors. In some embodiments, photoreceptor death and/or apoptosis is caused by retinal detachment, age-related macular degeneration, trauma, cancer, tumor, inflammation, uveitis, diabetes, hereditary retinal degeneration, and/or a disease affecting photoreceptor cells. In some embodiments, photoreceptor death and/or apoptosis is caused by retinal detachment. In some embodiments, retinal detachment is caused by one or more underlying diseases, disorders, or conditions (e.g., age-related macular degeneration, trauma, cancer, tumor, inflammation, uveitis, diabetes, hereditary retinal degeneration, etc.). In some embodiments, the present invention finds utility in enhancing photoreceptor viability and/or inhibiting photoreceptor death in a variety of conditions and/or diseases including, but not limited to macular degeneration (e.g. dry, wet, non-exudative, or exudative/neovascular), ocular tumors, hereditary retinal degenerations (e.g. retinitis pigmentosa, Stargardt's disease, Usher Syndrome, etc), ocular inflammatory disease (e.g. uveitis), ocular infection (e.g. bacterial, fungal, viral), autoimmune retinitis (e.g. triggered by infection), trauma, diabetic retinopathy, choroidal neovascularization, retinal ischemia, retinal vascular occlusive disease (e.g. branch retinal vein occlusion, central retinal vein occlusion, branch retinal artery occlusion, central retinal artery occlusion, etc.), pathologic myopia, angioid streaks, macular edema (e.g. of any etiology), and/or central serous chorioretinopathy.

In some embodiments, the present invention comprises administration of a composition to inhibit photoreceptor death (e.g. apoptosis). In some embodiments, a composition comprises a pharmaceutical, small molecule, peptide, nucleic acid, molecular complex, etc. In some embodiments, a composition enhances the expression, activity, transport, and/or downstream effects of Faim2. In some embodiments, a composition inhibits degradation of Faim2, a regulator thereof, or a downstream target.

In some embodiments, the present invention provides administration of a photoreceptor protective polypeptide to inhibit photoreceptor apoptosis. In some embodiments, a polypeptide of the present invention can be prepared by methods known to those of ordinary skill in the art. For example, the claimed polypeptide can be synthesized using solid phase polypeptide synthesis techniques (e.g. Fmoc). Alternatively, the polypeptide can be synthesized using recombinant DNA technology (e.g., using bacterial or eukaryotic expression systems). Accordingly, to facilitate such methods, the present invention provides genetic vectors (e.g., plasmids) comprising a sequence encoding the inventive polypeptide, as well as host cells comprising such vectors. Furthermore, the invention provides the polypeptide produced via recombinant methods.

In some embodiments, the present invention provides administration of photoreceptor protective compositions (e.g. photoreceptor protective peptides, polypeptide, small molecules, nucleic acids, nucleic acids encoding protective peptides, etc.). In some embodiments, the present invention provides administration of polypeptides which inhibit apoptosis of photoreceptor cells (e.g. Faim2 and/or fragments thereof, etc.). In some embodiments, the present invention provides administration of nucleic acids which encode polypeptides (e.g. Faim2 and/or fragments thereof, etc.) which inhibit apoptosis of photoreceptor cells. In some embodiments, administered compositions inhibit one or more apoptotic pathways. In some embodiments, a Faim2 polypeptide (e.g., full length Faim2, wild-type Faim2, mutant Faim2, truncated Faim2, etc.) is administered (e.g. to a subject, cell or cells) as an inhibitor of apoptosis and/or photoreceptor protective peptide. In some embodiments, a Faim2 polypeptide is administered. In some embodiments, a polypeptide with at least 50% homology to Faim2 or a fragment is administered (e.g. at least 60% homology, at least 70% homology, at least 80% homology, at least 90% homology, at least 95% homology, at least 99% homology, etc.).

In some embodiments, the present invention provides peptide fragments of Faim2. In some embodiments, the present invention provides one or more peptide fragments of Faim2 that retain all or a portion of the antiapoptotic and/or photoreceptor protective functions of Faim2. In some embodiments, a Faim2 fragment comprises a fragment of wild-type Faim2. In some embodiments, a Faim2 fragment comprises at least 50% homology to a portion of Faim2 (e.g. at least 60% homology, at least 70% homology, at least 80% homology, at least 90% homology, at least 95% homology, at least 99% homology, etc.). In some embodiments a Faim2 peptide fragment is 5-315 amino acids in length (e.g., 5, 6, 7, 8, 9, 10, 11, 12, 13, 14, 15 . . . 20 . . . 25 . . . 30 . . . 40 . . . 50 . . . 75 . . . 100 . . . 150 . . . 200 . . . 300 . . . 315). In some embodiments, a Faim2 peptide fragment comprises the C-terminal portion of Faim2. In some embodiments, a Faim2 peptide fragment comprises a central portion of Faim2. In some embodiments, a Faim2 peptide fragment comprises the N-terminal portion of Faim2.

In some embodiments, polypeptides (e.g., Faim2 polypeptides) or peptide fragments (e.g., fragments of Faim2) are isolated and/or purified (or substantially isolated and/or substantially purified). Accordingly, the invention provides polypeptides and/or peptides in substantially isolated form. In some embodiments, polypeptides and/or peptides are isolated from other polypeptides and polypeptide as a result of solid phase protein synthesis, for example. Alternatively, polypeptides and/or peptides can be substantially isolated from other proteins after cell lysis from recombinant production. Standard methods of protein purification (e.g., HPLC) can be employed to substantially purify polypeptides.

In some embodiments, the present invention provides a preparation of Faim2 polypeptides or Faim2 peptide fragments in a number of formulations, depending on the desired use. For example, where the polypeptide or peptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc., and the inventive polypeptide can, in some embodiments, be prepared in lyophilized form. Moreover, such preparations can include other desired agents, such as small molecules or even other polypeptides and proteins, if desired. Indeed, the invention provides such a preparation comprising a mixture of different embodiments of the inventive polypeptide (e.g., a plurality of polypeptide species as described herein).

In some embodiments, the present invention also provides a pharmaceutical composition comprising of one or more polypeptides (e.g., Faim2 or mutants thereof), peptides (e.g., Faim2 fragments), and/or mixtures thereof and a pharmaceutically acceptable carrier. Any carrier which can supply a polypeptide without destroying the vector within the carrier is a suitable carrier, and such carriers are well known in the art. The composition can be formulated for local (e.g., ocular; intraocular space; etc.), parenteral, oral, or topical administration. For example, a parenteral formulation could consist of a prompt or sustained release liquid preparation, dry powder, emulsion, suspension, or any other standard formulation. An oral formulation of the pharmaceutical composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or tissue or other affected areas, such as dimethylsulfoxide and related analogs. The pharmaceutical composition could also be delivered topically using a transdermal device, such as a patch or pump, which could include the composition in a suitable solvent system with an adhesive system, such as an acrylic emulsion, and a polyester patch. Compositions could be delivered via eye drops or other topical eye delivery method. Compositions may be delivered intraocularly, anywhere in the eye including, for example, the vitreous cavity, the anterior chamber, etc. Compisitions may be delivered intravitrealy as is commonly done with intravitreal injections of Lucentis (ranabizumab), Avastin (bevazizumab), triamcinolone acetonide, antibiotics, etc. Compositions may be delivered periocularly (e.g. to the tissue around the eyeball (globe) but within the bony orbit). Compositions may be delivered via intraocular implant (e.g. gancyclovir implant, fluocinolone implant, etc.). In intraocular implant delivery, devices containing compositions of the present invention are surgically implanted (e.g. within the vitreous cavity), and the drug is released into the eye (e.g. at a predetermined rate). Compositions may be administered using encapsulated cell technology (e.g. by Neurotech) in which genetically modified cells are engineered to produce and secrete compositions of the present invention (e.g. Faim2, mutants thereof, fragments thereof, etc.). Compositions may be delivered via transcleral drug delivery using a device sutured or placed next to the globe that would slowly elute the drug, which would then diffuse into the eye.

In some embodiments, the present invention provides co-administration of two or more anti-apoptotic and/or photoreceptor protective compositions described herein. In some embodiments, the present invention provides co-administration of one or more anti-apoptotic and/or photoreceptor protective compositions described herein with one or more additional pharmaceutical compositions for treatment of conditions (e.g., retinal detachment) described herein.

In some embodiments, the invention provides a method of employing polypeptides to attenuate the activation of one or more members of the TNFR superfamily, desirably Fas and/or TNFR in photoreceptors and/or retinas. In some embodiments, such method is employed, for example, to inhibit cell death (e.g., apoptosis) in cells and tissues, and it can be employed in vivo, ex vivo or in vitro. Thus, the invention provides for the use of the Faim polypeptide (e.g., Faim2, Faim2 mutants, Faim2 fragments, etc.) for attenuating cell death (e.g. retinal cell death) in accordance with such methods. For in vitro application, the polypeptide (e.g., Faim2, Faim2 mutants, Faim2 fragments, etc.) is provided to cells, typically a population of cells (e.g., within a suitable preparation, such as a buffered solution) in an amount and over a time course sufficient to inhibit apoptosis within the cells or to inhibit inflammation. If desired, a controlled population untreated with the inventive polypeptide can be observed to confirm the effect of the inventive polypeptide in reducing the inhibition of cell death or inflammation within a like population of cells.

In some embodiments, methods of the present invention are employed in vivo. In some embodiments, polypeptides (e.g., Faim2, Faim2 mutants, Faim2 fragments, etc.) are delivered to a human or animal subject in an amount and at a location sufficient to inhibit or attenuate apoptosis or inflammation within the patient (e.g., within desired tissue). Polypeptide (e.g., Faim2, Faim2 mutants, Faim2 fragments, etc.) can be formulated into a suitable pharmaceutical composition (e.g., as described above or as otherwise known to those of ordinary skill in the art) for delivery into the subject. The delivery can be local (e.g., by injection or implantation within the desired tissue to be treated) or systemic (e.g., by intravenous or parenteral injection).

In some embodiments, the present invention provides a method for treating patients suffering from such retinal detachment and or retinal disorders and in need of treatment. In some embodiments, a pharmaceutical composition comprising at least one polypeptide of the present invention (e.g., Faim2, Faim2 mutants, Faim2 fragments, etc.) is delivered to such a patient in an amount and at a location sufficient to treat the disorder or disease. In some embodiments, polypeptides of the present invention (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application of the inventive method of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to a degree ascertainable.

In some embodiments, the present invention provides methods for increasing photoreceptor survival comprising administering a photoreceptor protective pharmaceutical composition (e.g., Faim2, Faim2 mutants, Faim2 fragments, mimic of Faim2 function (e.g., small molecule mimitec), etc.). The pharmaceutical compound may be administered in the form of a composition which is formulated with a pharmaceutically acceptable carrier and optional excipients, adjuvants, etc. in accordance with good pharmaceutical practice. The photoreceptor protective pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. eye drops, injection, etc.), the composition form is determined. In general, it is preferred to use a unit dosage form of the inventive inhibitor in order to achieve an easy and accurate administration of the active pharmaceutical compound. In general, the therapeutically effective pharmaceutical compound is present in such a dosage form at a concentration level ranging from about 0.5% to about 99% by weight of the total composition: i.e., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, a photoreceptor protective pharmaceutical composition in a unit dosage form for administration to a subject, comprising a pharmaceutical compound and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

In some embodiments, photoreceptor protective compositions of the present invention (e.g., comprising Faim2, fragments thereof, mutants thereof, or mimitecs thereof) are administered optically, for example, using the techniques described herein, and/or other techniques (e.g. injection, topical administration, etc.) known to those in the art (See, e.g., Janoria et al. Expert Opinion on Drug Delivery. July 2007, Vol. 4, No. 4, Pages 371-388; Ghate & Edelhauser. Expert Opin Drug Deliv. 2006 March; 3(2):275-87; Bourges et al. Adv Drug Deliv Rev. 2006 November 15; 58(11):1182-202. Epub 2006 Sep. 22; Gomes Dos Santos et al. Curr Pharm Biotechnol. 2005 February; 6(1):7-15; herein incorporated by reference in their entireties).

In some embodiments, photoreceptor protective compositions (e.g., Faim2, fragments, thereof, mimitecs thereof, mutants thereof, etc.) are provided as part of a kit. In some embodiments, a kit of the present invention comprises one or more photoreceptor protective compositions and/or photoreceptor protective pharmaceutical compositions. In some embodiments, a kit comprises a photoreceptor protective composition is configured for co-administration with one or more additional compositions (e.g. pharmaceutical compositions). In some embodiments, one or more photoreceptor protective compositions are co-administered with one or more other agents for effective protection of photoreceptors and/or inhibition of apoptosis.

In some embodiments, the present invention provides compositions and methods to upregulate and/or enhance the expression of Faim2 (or mutants or fragments thereof) in a cell or subject. In some embodiments, compositions that enhance the activity of Faim2 (or mutants or fragments thereof) are administered to a cell of subject. In some embodiments, regulators of Faim2 expression, activity, and/or degradation are inhibited or activated to result in increased Faim2 concentration or activity. In some embodiments, compositions are provided (e.g., small molecules) to active or inhibit Faim2, a regulator thereof, or a downstream target thereof, in order to provide an anti-apoptotic and/or photoreceptor-protective effect.

In some embodiments, the present invention provides compositions and method to perform assays to screen for one or more of: functional portions of Faim2 (e.g., Faim2 fragments), regulators of Faim2 expression, regulators of Faim2 activity, regulators of Faim2 degradation, regulators of proteins that are functionally associated with Faim2 (e.g., ERK, proteins downstream of Faim2, proteins upstream of Faim2), small molecules effectors of Faim2 expression, function, and/or activity, etc.

EXPERIMENTAL

Example 1

Compositions and Methods

Experimental Model of Retinal Detachment

All experiments were conducted in accordance with the ARVO Statement for the Use of Animals in Ophthalmic and Vision Research and the guidelines established by the University Committee on Use and Care of Animals of the University of Michigan. Detachments were created in adult male Brown-Norway rats (300-400 g) (Charles River Laboratories, Wilmington, Mass.) (Zacks et al. *Invest Ophthalmol Vis Sci* 2003; 44:1262-1267; herein incorporated by reference in its entirety). Rodents were anesthetized with a 50:50 mix of ketamine and xylazine, and pupils were dilated with topical phenylephrine (2.5%) and tropicamide (1%). A 20-gauge microvitreoretinal blade was used to create a sclerotomy 2 mm posterior to the limbus, carefully avoiding lens damage. A Glaser subretinal injector (32-gauge tip; BD Ophthalmic Systems, Franklin Lakes, N.J.) was introduced through the sclerotomy into the vitreous cavity and then through a peripheral retinotomy into the subretinal space. Sodium hyaluronate (10 mg/mL) (Abbott Medical Optics, Healon OVD) was slowly injected to detach the neurosensory retina from the underlying retinal pigment epithelium. Approximately one-third to one-half of the neurosensory retina was detached. Detachments were created in the left eye. The right eye served as the control, with all the steps of the procedure performed except for introduction of the subretinal injector and injection of the sodium hyaluronate.

Cell Culture

The 661W cell line was maintained in Dulbecco's modified Eagle's medium containing 10% fetal bovine serum, 300 mg/L glutamine, 32 mg/L putrescine, 40 μL/L of β-mercaptoethanol, and 40 μg/L of both hydrocortisone 21-hemisuccinate and progesterone. The media also contained penicillin (90 units/mL) and streptomycin (0.09 mg/mL). Cells were grown at 37° C. in a humidified atmosphere of 5% $CO_2$ and 95% air.

Western Blot Analysis

Retinas from experimental eyes with detachments and control eyes without detachments were dissected from the RPE-choroid, homogenized, and lysed in buffer containing 10 mM HEPES (pH 7.6), 0.5% IgEPal, 42 mM KCl, 1 mM phenylmethylsulfonyl fluoride (PMSF), 1 mM EDTA, 1 mM EGTA, 1 mM dithiothreitol (DTT), and 5 mM MgCl$_2$ and 1 tablet of protease inhibitors per 10 mL buffer (Complete Mini; Roche Diagnostics GmbH, Madison, Wis.). 661W cells were lysed and homogenized in lysis buffer (as above). The homogenates were incubated on ice and centrifuged at 22,000 g at 4° C. for 60 minutes. The protein concentration of the supernatant was then determined (DC Protein Assay kit; Bio-Rad Laboratories, Hercules, Calif.). The protein samples were separated on SDS-polyacrylamide gels (Tris-HCl Ready Gels; Bio-Rad Laboratories, Hercules, Calif.). After electrophoretic separation, the proteins were transferred onto polyvinylidene fluoride (PVDF) membranes (Immobilon-P; Millipore, Billerica, Mass.). Protein bands were visualized with Ponceau S staining, and the lanes were assessed for equal loading by densitometry of entire lanes. Membranes were then immunoblotted with antibodies according to the manufacturer's instructions. The following antibodies were used: Faim2/LFG (Anaspec, Fremont, Calif.), P-JNK, JNK, P-ERK, ERK, P-c-Jun (Cell Signaling, Danvers, Mass.), Actin (Santa Cruz Biotechnology, Santa Cruz, Calif.). Densitometry measurements were performed using ImageJ software available from the National Institutes of Health.

Caspase Assays

Caspase 8 and Caspase 3 activity were measured by a commercially available luminescent tetrapeptide cleavage assay kits (Promega, Madison, Wis.). The 661W cells were seeded in 96-well plates (Nunc, Rochester, N.Y.) at 1000-1500 cells/well for 24 hours prior to treatment or siRNA transfection. Cells were treated with 500 ng/mL of Fas-agonistic Jo2 monoclonal antibody (BD Biosciences, Franklin Lakes, N.J.). In some experiments, cells were pretreated with MEK inhibitor U0126, JNK inhibitor SP600125, or DMSO. Caspase activity was measured at various time points by incubating the cells with the pro-luminescent substrate in 96-well plates following manufacturer's instructions. Controls included untreated cells and wells with no cells. Luminescence was measured in a plate reader luminometer (Turner Biosystems, Sunnyvale, Calif.).

Cell Viability

Cell viability was measured by a commercially available luminescent assay kit (Promega, Madison, Wis.). The 661W cells were seeded in 96-well plates (Nunc, Rochester, N.Y.) at 1000-1500 cells/well for 24 hours prior to treatment. Cells were treated with 500 ng/mL of Fas-agonistic Jo2 monoclonal antibody (BD Biosciences, Franklin Lakes, N.J.). In some experiments, cells were pretreated with MEK inhibitor U0126, JNK inhibitor SP600125, or DMSO. Cell viability was measured at various time points by incubating the cells with the pro-luminescent substrate in 96-well plates following manufacturer's instructions. Controls included untreated cells and wells with no cells. Luminescence was measured in a plate reader luminometer (Turner Biosystems, Sunnyvale Calif.).

siRNA Treatment 661W cells were treated with small inhibitory RNAs against mouse Faim2 (siFaim2, Invitrogen Life Technologies, Carlsbad, Calif.) to prevent Fas-induced increase in the transcription of Faim2 gene. siFaim2 or control siRNA (labeled with Cy3) were transfected into cells using Lipofectamine RNAiMax (Invitrogen Life Technologies, Carlsbad, Calif.) according to manufacturer's instructions. siRNA transfection efficiency was determined by direct examination of Cy3-labeled control siRNA uptake in cells using an inverted fluorescent microscope. Cells were treated 36-48 hours after siRNA transfection.

Example 2

Retinal Detachment Induces Faim2 Expression

Microarray analysis of genes expressed upon experimental retinal detachment identified Faim2 gene as a transcript that is induced at 24 hours post retina-RPE separation. To supplement the microarray data, the level of Faim2 protein in detached rat retinas was evaluated. Levels of Faim2 started to increase by 8 hours of retinal detachment (SEE FIG. 1A), and remained elevated after seven days. Faim2 expression data was consistent with microarray data, both demonstrating that retinal detachment leads to increased levels of Faim2.

Example 3

Fas Signaling Leads to Elevated Faim2 Expression in 661W Cells

Experiments were conducted during development of embodiments of the present invention to determine whether the Faim2 increase in the in vivo model of experimental retinal detachment could be reproduced using our in vitro model of Fas-mediated photoreceptor apoptosis. The 661W cell line is a photoreceptor line that has been immortalized by the expression of SV40-T antigen under control of the human interphotoreceptor retinol-binding protein (IRBP) promoter (al-Ubaidi et al. *J Cell Biol* 1992; 119:1681-1687; herein incorporated by reference in its entirety). 661W cells express cone photoreceptor markers, including blue and green cone pigments, transducin, and cone arrestin (Tan et al. *Investigative ophthalmology & visual science* 2004; 45:764-768; herein incorporated by reference in its entirety). Treatment of 661W cells with an antibody that activates the Fas-receptor (Fas-activating antibody or Fas-AAb) leads to caspase 8 activation and apoptosis, confirming that Fas death receptor signaling is intact in 661W cells (Besirli et al. *Invest Ophthalmol Vis Sci* 2010; 51:2177-2184; herein incorporated by reference in its entirety). Treatment of 661W cells with Fas-AAb, resulted in significantly increased Faim2 expression (FIG. 1B), demonstrating that, similar to the in vivo results, direct activation of Fas receptor signaling in 661W photoreceptors leads to elevated Faim2 levels in the experimental retinal detachment.

Example 4

Figure 2:
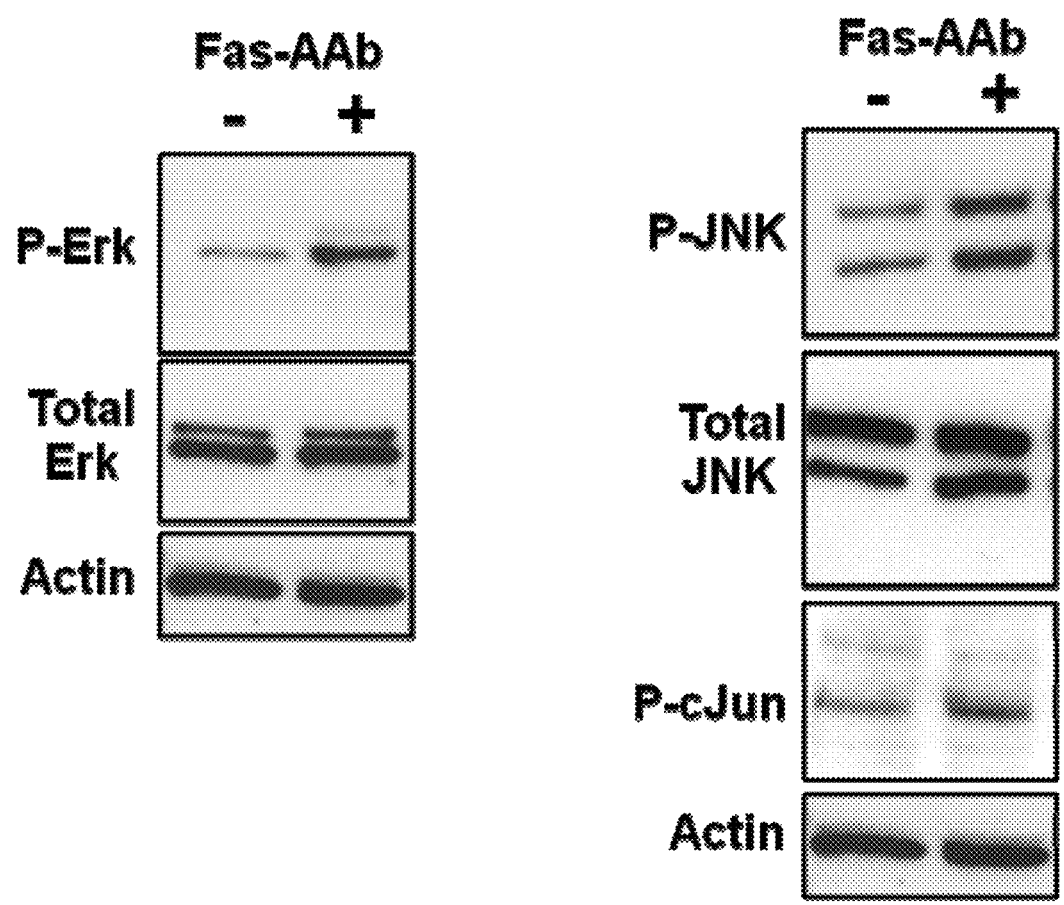
FIG. 2 shows ERK and JNK stress kinase pathways are activated in Fas-exposed photoreceptors. Activation of ERK and JNK signaling was analyzed in 661W cells treated with 500 ng/mL of Fas-activating antibody (Fas-AAb) by immunoblotting. ERK signaling was evaluated by phospho-p44/42 (P-ERK) antibody and JNK signaling by measuring levels of phospho-JNK (P-JNK) and phospho-c-Jun (P-c-Jun) after 4 hours of Fas-AAb treatment. Levels of total ERK and total JNK remained stable, suggesting specific conversion of existing kinases to their phosphorylated form. Actin is shown as loading control.

661W Cells Show Increased ERK and JNK Signaling Following Fas Pathway Activation Increased ERK and JNK signaling in detached rodent retinas has been detected by increased levels of phosphorylated forms of these stress kinases (Zacks. *Trans Am Ophthalmol Soc* 2009; 107:343-382; herein incorporated by reference in its entirety). Experiments were conducted during development of embodiments of the present invention to determine whether exogenous activation of Fas signaling could lead to MAPK activation in 661W cells. When 661W cells were treated with the Fas-AAb, both ERK and JNK phosphorylation increased significantly (SEE FIG. 2). The levels of total ERK and JNK remained stable after Fas-AAb treatment, indicating that Fas signaling induces conversion of these stress kinases from the existing inactive form to phosphorylated active form. Further evidence of JNK activation was demonstrated by increased phosphorylation of one of its downstream targets, transcription factor c-Jun (SEE FIG. 2).

Example 5

Inhibition of Stress Kinases Enhances Fas-Mediated Photoreceptor Apoptosis

Figure 3:
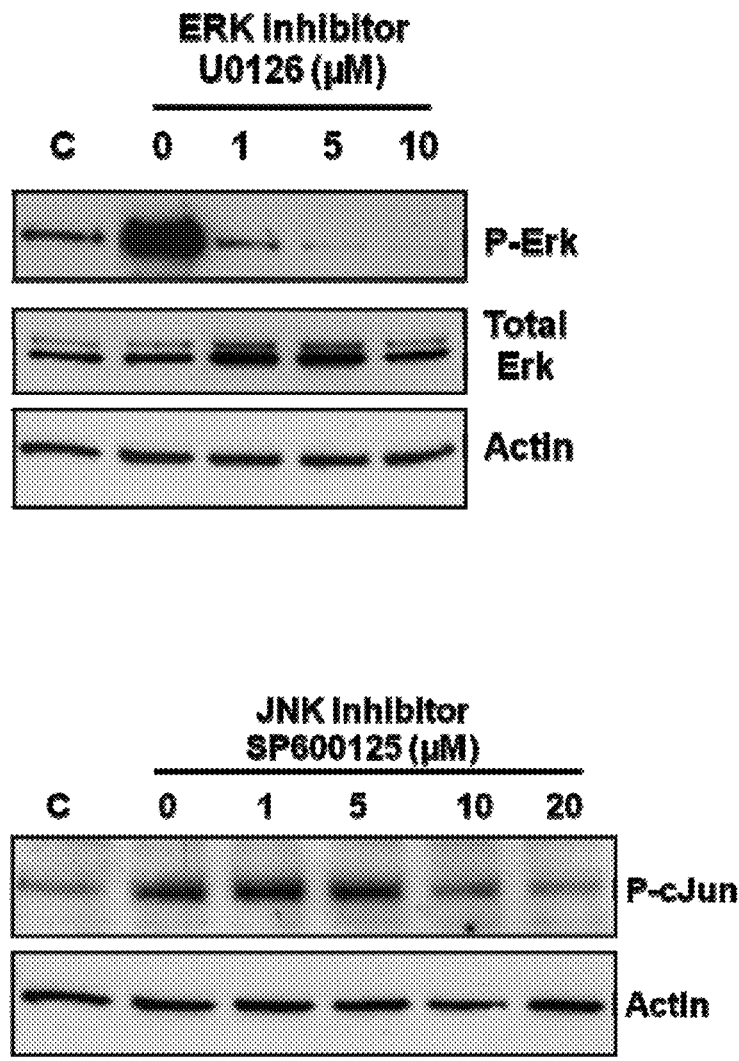
FIG. 3 shows U0126 and SP600125 inhibit ERK and JNK signaling in Fas-AAb treated 661W cells. Cells were pre-treated with the inhibitors 1 hour prior to Fas-AAb addition. Protein was isolated 4 hours later and levels of P-ERK, total ERK, and P-c-Jun were determined by immunoblotting. C: Untreated controls (No Fas-AAb). Actin is shown as loading control.

MAPKs play differential roles during cellular apoptosis depending on the context. In general, ERK signaling is important for activating pro-survival signals, whereas JNK signaling tends to be pro-apoptotic. To test the role of ERK and JNK signaling, specific and differential inhibitors of ERK and JNK phosphorylation were utilized. To reduce ERK activity, its upstream activator, MEK, was inhibited with U0126. JNK signaling was reduced by a direct JNK inhibitor, SP600125. U0126 was effective in preventing the Fas-AAb-induced phosphorylation of ERK starting at low doses, with maximal inhibition at 10 μM (SEE FIG. 3). Similarly, SP600125 blocked Fas-AAb-dependent phosphorylation of JNK-target c-Jun, with maximal effect seen at the 10-20 μM concentration level (SEE FIG. 3).

Figure 4A:
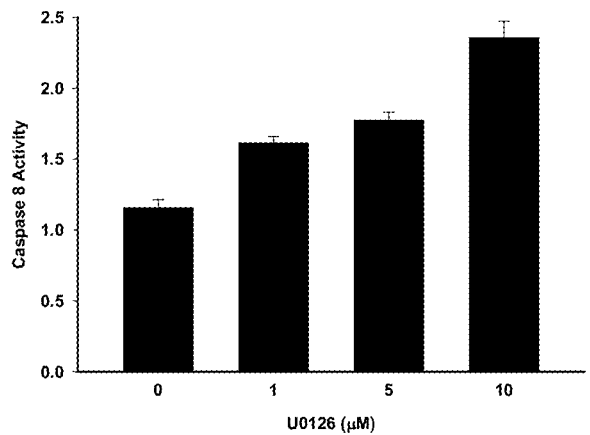
FIG. 4 shows inhibition of ERK or JNK signaling increases Fas-mediated caspase activation and photoreceptor apoptosis. A) Activation of caspase 8 and caspase 3 were evaluated in the presence of U0126 after 24 hours of Fas-AAb treatment. The effect of ERK inhibitor on Fas-mediated photoreceptor apoptosis was determined in 661W cells, n=8, mean±SE. B) Activation of caspase 8 and caspase 3 were evaluated in the presence of SP600125 after 24 hours of Fas-AAb treatment, n=8, mean±SE. The effect of SP600125 on Fas-mediated photoreceptor apoptosis was determined in 661W cells.
Figure 4A:
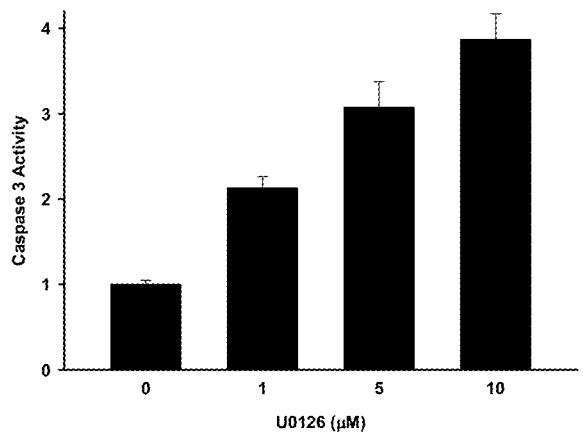
Figure 4A:
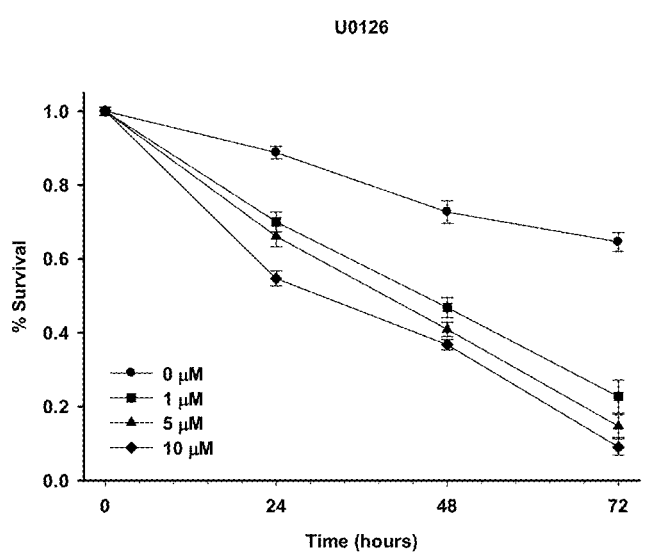
Figure 4B:
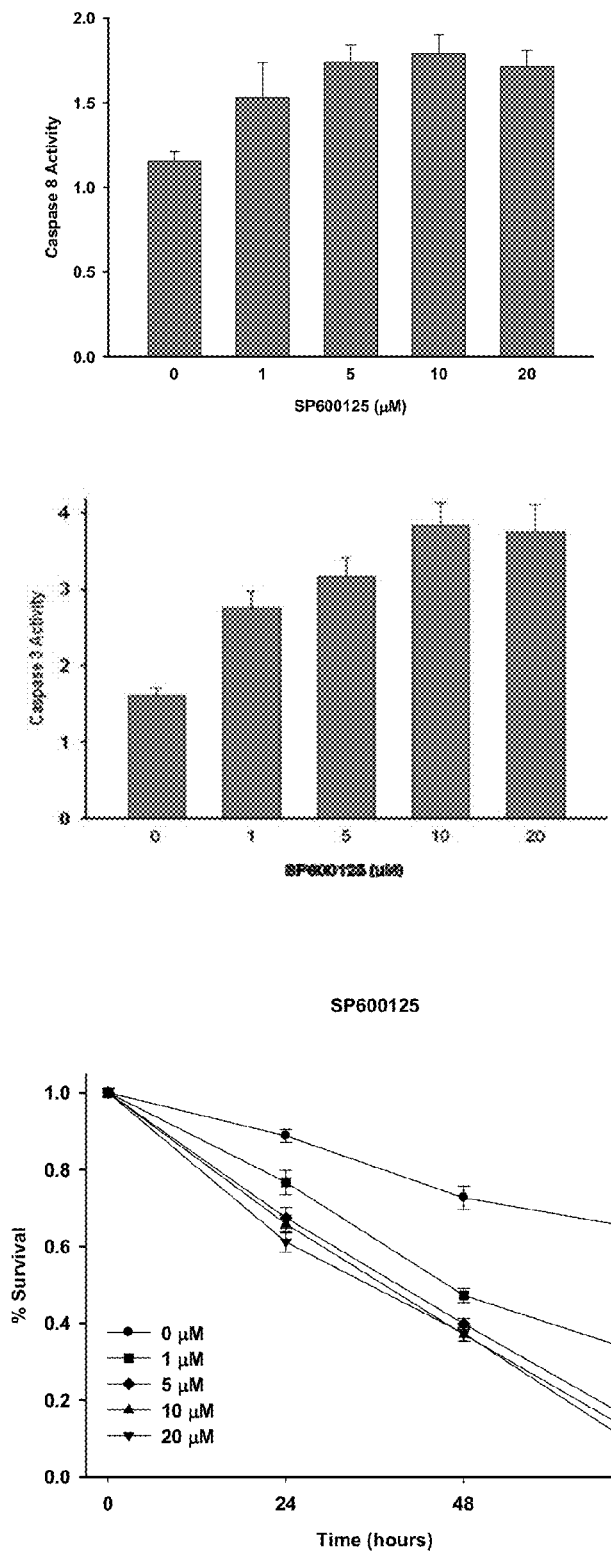

It was demonstrated when cells were exposed to Fas-AAb in the presence of U0126, there was a dose-dependent increase in caspase 8 and caspase 3 activity (FIG. 4A), thereby demonstrating the effect of blocking MAPK signaling on Fas-mediated apoptosis of 661W cells. Similarly, U0126 treatment increased Fas-AAb-mediated cell death (SEE FIG. 4A). This dose dependence was consistent with the dose of inhibitor found to block ERK phosphorylation seen with immunoblotting. Similar findings were observed with inhibition of the JNK pathway. SP600125 increased caspase 8 and caspase 3 activities in a dose-dependent manner (SEE FIG. 4B). 661W cells were more sensitive to Fas-mediated cell death when JNK signaling was blocked with SP600125 (SEE FIG. 4B). These findings strongly indicate that both ERK and JNK signaling pathways are important in activating survival pathways in photoreceptors undergoing Fas-mediated apoptosis.

Example 6

Faim2 Expression is Regulated by ERK Signaling

Figure 5:
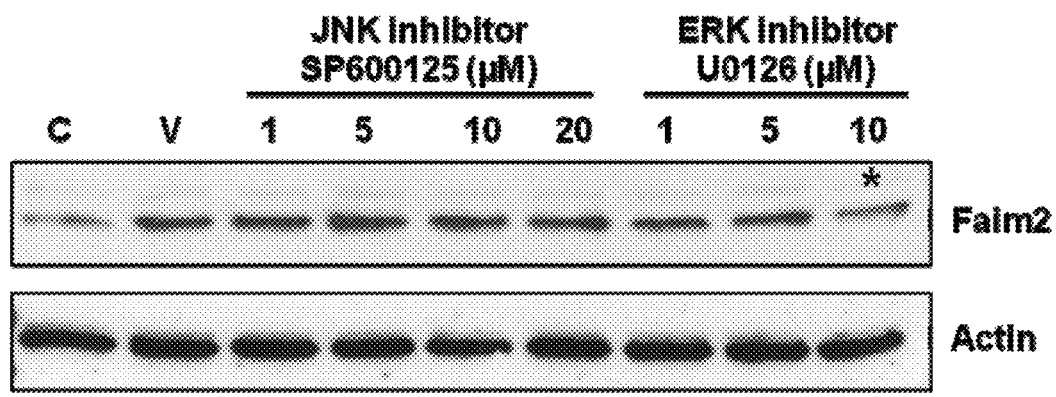
FIG. 5 shows Faim2 expression is regulated by ERK signaling. 661W cells were treated with Fas-AAb with or without MAPK inhibitors and levels of Faim2 were determined by immunoblotting. The JNK inhibitor SP600125 did not affect Faim2 levels, while the ERK inhibitor U0126 showed a dose-dependent inhibition of the increase in Faim2 levels normally seen after treatment with the Fas-activating antibody. Densitometry showed a significant decrease in Faim2 level with 10 µM dose of U0126 (*). This is consistent with 10 µM concentration of U0126 being the maximally-effective dose for suppressing ERK phosphorylation and increasing caspase 8 and caspase 3 activity. C: Untreated controls (No Fas-AAb), V: Vehicle only control (DMSO).

Experiments were conducted during development of embodiments of the present invention to test whether the ERK or JNK pathway regulate photoreceptor survival by controlling Faim2 levels after Fas-receptor activation. Faim2 expression was analyzed in 661W cells when they were treated with Fas-AAb in the presence of MAPK inhibitors. Inhibition of the ERK pathway with U0126 reduced the levels of Faim2 in 661W cells (SEE FIG. 5). In contrast, JNK inhibitor SP600125 did not show any effect on Faim2 expression in Fas-treated cells SEE FIG. 5). These results demonstrate that ERK signaling is important in upregulation of Faim2 during photoreceptor apoptosis, whereas JNK pathway has no detectable effect.

Example 7

Reduced Faim2 Expression Enhances Fas-Mediated Photoreceptor Apoptosis

Figure 6:
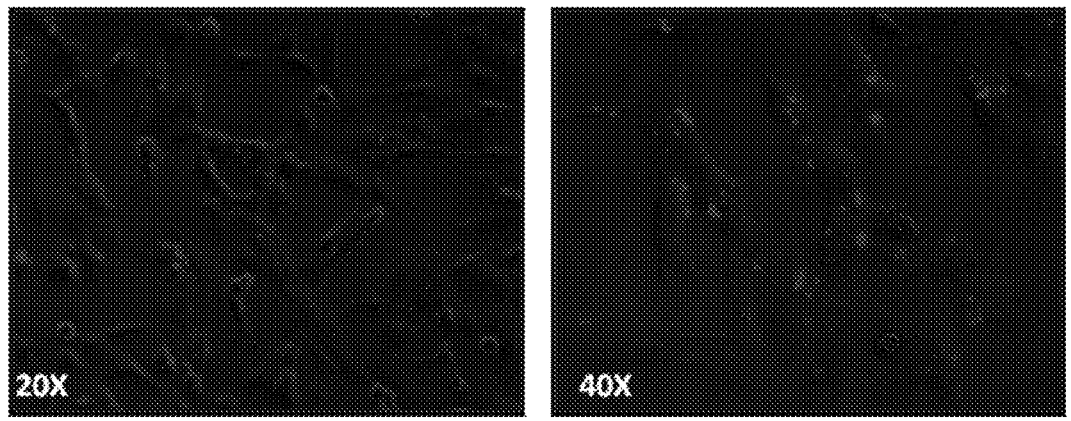
FIG. 6 shows siRNA-mediated knock down of Faim2 expression enhances Fas-mediated photoreceptor apoptosis. A) siRNA transfection efficiency in 661W cells was determined by transfecting cells with various concentrations of control siRNA labeled with Cy3. Fluorescent microscopy was used to visualize cells and siRNA molecules after 24 hours. Photos show intracellular punctate red fluorescence respresenting siRNAs taken up by cells. B) siFaim2 reduced Faim2 protein levels in 661W cells. Cells were transfected with siFaim or siControl and treated with 500 ng/ml of Fas-AAb after 36 hours. Levels of Faim2 were determined by immunoblotting after 4 hours of Fas-AAb treatment. C) Caspase 8 activation was increased in 661W cells after Faim2 knock down. Cells were treated with Fas-AAb 36 hours after siFaim transfection. Caspase 8 levels were determined at 12 and 24 hours.
Figure 6:
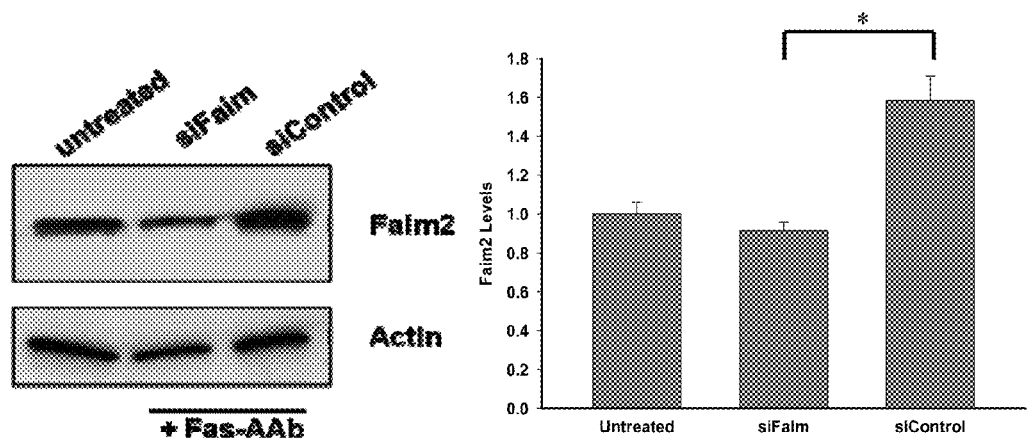
Figure 6:
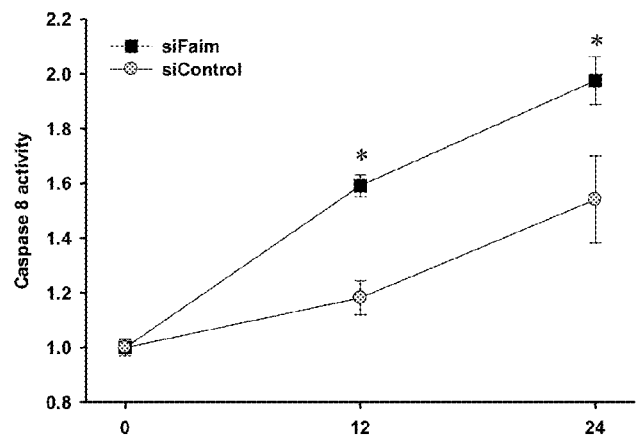

A loss-of-function experiment was performed during development of embodiments of the present invention to determine whether an increase in Faim2 levels acts as an inhibitor of apoptosis. Small inhibitory RNA (siRNA) was used to reduce Faim2 expression levels in 661W cells. The effectiveness of siRNA transfection in 661W cells was analyzed using a control siRNA (siControl) labeled with a fluorescent tag, Cyanine 3 (Cy3). Analysis of various siRNA concentrations demonstrated that 20 nM of siRNA resulted in the best transfection efficiency as determined by the uptake of Cy3-labeled siRNA by 661W cells (SEE FIG. 6A). Transfection of 661W cells was performed using siRNAs against Faim2 mRNA (siFaim). 661W cells transfected with siFaim showed reduced levels of Faim2 protein after Fas-AAb treatment (SEE FIG. 6B). This decline in protein expression was not seen in cells transfected with the control siRNA (siControl). The effect of Faim2 knock down on Fas-mediated photoreceptor apoptosis was evaluated. In siFaim transfected cells, Fas-AAb treatment resulted in more robust caspase 8 activation compared with cells transfected with control siRNA (SEE FIG. 6C). This caspase activation occurred earlier and peaked at a significantly higher level when Faim2 expression was reduced in 661W photoreceptor cells with siFaim (SEE FIG. 6C). These results demonstrate that Faim2 acts an anti-apoptotic factor in photoreceptors and Faim2 function is critical for blocking early caspase 8 activation.

Example 8

Evaluation of Protective Effect of Faim2 Polypeptides

Experiments to evaluate the ability of Faim2 polypeptide (or fragments thereof) gene therapy to provide anti-apoptotic and/or photoreceptor protective effect to cells following retinal detachment are carried out according to established protocol (Zadro-Lamoureux et al. Investigative Ophthalmology & Visual Science, Vol. 50, No. 3, 2009; herein incorporated by reference in its entirety). The Faim2 gene and/or a gene expressing a Faim2 fragment or Faim2 mutant is placed in a recombinant adeno-associated virus (AAV) vector behind a promoter that enables increased expression of the Faim2 polypeptide or peptide. The vector is transplanted subretinally into the eye of a test subject (e.g., rat). Retinal detachments are then created at the site of viral injection. Histologic and other analysis is conducted on samples taken at various times following the detachment to confirm the presence and expression of the Faim2 polypeptide (or mutant of fragment thereof), and to assess levels of apoptosis and changes in retinal thickness.

We claim:

1. A method of increasing photoreceptor survival comprising administering to the retina of a subject a nucleic acid encoding a polypeptide or peptide with at least 90% identity to SEQ ID NO: 1 (wild-type Fas apoptotic inhibitory molecule 2 (Faim2)) that elicits the Faim2 antiapoptotic pathway.

2. The method of claim 1, wherein said increasing photoreceptor survival comprises inhibiting photoreceptor apoptosis.

3. The method of claim 2, wherein said photoreceptor apoptosis comprises FAS-mediated photoreceptor apoptosis.

4. The method of claim 1, wherein said polypeptide or peptide is full-length of Faim2.

5. The method of claim 1, wherein said polypeptide or peptide is a fragment of full-length Faim2.

6. The method of claim 5, where said polypeptide or peptide maintains the anti-apoptotic and/or photoreceptor protective functionality of full-length Faim2.

7. The method of claim 1, wherein said nucleic acid is administered to a population of cells.

8. The method of claim 1, wherein said subject suffers from an ocular condition, disease, or condition or disease affecting ocular health selected from the list consisting of retinal detachment, macular degeneration, retinitis pigmentosa, ocular inflammation, autoimmune retinopathy, trauma, cancer, tumor, uveitis, hereditary retinal degeneration, diabetic retinopathy, choroidal neovascularization, retinal ischemia, pathologic myopia, angioid streaks, macular edema, or central serous chorioretinopathy.

9. The method of claim 1, wherein said nucleic acid is within a genetic vector.

10. The method of claim 9, wherein said genetic vector further comprises a promoter that enables increased expression of the polypeptide or peptide encoded by the nucleic acid.

11. The method of claim 10, wherein said genetic vector is an adeno-associated virus (AAV) vector.

12. The method of claim 1, wherein said nucleic acid is administered subretinally.

13. The method of claim 12, wherein said nucleic acid is administered to photoreceptor cells.

* * * * *